(12) United States Patent
Sharma (10) Patent No.: US 12,390,102 B2
(45) Date of Patent: Aug. 19, 2025

(54) GENERATING AND EVALUATING TWO- AND THREE-DIMENSIONAL IMAGES OF THE INTERIOR OF AN EYE

(71) Applicant: Alcon Inc., Fribourg (CH)

(72) Inventor: Utkarsh Sharma, Solon, OH (US)

(73) Assignee: Alcon Inc., Fribourg (CH)

( * ) Notice: Subject to any disclaimer, the term of this patent is extended or adjusted under 35 U.S.C. 154(b) by 409 days.

(21) Appl. No.: 17/938,187

(22) Filed: Oct. 5, 2022

(65) Prior Publication Data
US 2023/0157536 A1    May 25, 2023

Related U.S. Application Data

(60) Provisional application No. 63/281,453, filed on Nov. 19, 2021.

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0058* (2013.01); *A61F 9/008* (2013.01); *G02B 26/101* (2013.01);
(Continued)

(58) Field of Classification Search
CPC ..... G02B 26/101; A61B 3/0058; A61B 3/102; A61F 9/008; A61F 9/00825;
(Continued)

(56) References Cited

U.S. PATENT DOCUMENTS

| | | |
|---|---|---|
| 3,780,979 A | 12/1973 | De Guillebon |
| 4,357,088 A | 11/1982 | Pomerantzeff |

(Continued)

FOREIGN PATENT DOCUMENTS

| | | |
|---|---|---|
| AU | 2018274939 B2 | 6/2020 |
| CN | 210009227 U | 2/2020 |

(Continued)

OTHER PUBLICATIONS

Damodaran et al., "Digital micromirror device based ophthalmoscope with concentric circle scanning", 2017, pp. 2766-2780, vol. 8, No. 5, Biomedical Optics Express.

(Continued)

*Primary Examiner* — Jack Dinh
(74) *Attorney, Agent, or Firm* — PATTERSON + SHERIDAN, LLP (57) ABSTRACT

In certain embodiments, an ophthalmic laser surgical system for imaging and treating a target in an eye includes an optical coherence tomography (OCT) device that: directs an imaging beam towards the eye; generates three-dimensional (3D) image data from the imaging beam reflected from the eye; and generates two-dimensional (2D) enface images from the 3D image data. The 2D enface images include a target enface image imaging the target in the eye and a retinal enface image imaging a shadow cast by the target onto the retina. An xy-scanner directs the imaging beam along an imaging beam path towards the eye, and directs a laser beam from the laser device along a laser beam path aligned with the imaging beam path towards the eye. A computer compares the target of the target enface image and the shadow of the retinal enface image to confirm the presence of the target.

23 Claims, 4 Drawing Sheets

(51) Int. Cl.
*A61F 9/008* (2006.01)
*G02B 26/10* (2006.01)
*G06T 7/13* (2017.01)
*G06T 7/60* (2017.01)
*G06T 7/73* (2017.01)

(52) U.S. Cl.
CPC .............. *G06T 7/13* (2017.01); *G06T 7/60* (2013.01); *G06T 7/73* (2017.01); *G06T 2207/10101* (2013.01); *G06T 2207/20216* (2013.01); *G06T 2207/30041* (2013.01)

(58) Field of Classification Search
CPC . A61F 2009/00851; A61F 2009/00874; G06T 7/13; G06T 7/73; G06T 2207/10101; G06T 2207/20216; G06T 2207/30041
See application file for complete search history.

(56) References Cited

U.S. PATENT DOCUMENTS

| | | | |
|---|---|---|---|
| 5,312,396 | A | 5/1994 | Feld |
| 5,909,270 | A | 6/1999 | Moser |
| 6,142,630 | A | 11/2000 | Koester |
| 6,322,556 | B1 | 11/2001 | Gwon |
| 6,789,900 | B2 | 9/2004 | Van De Velde |
| 7,374,287 | B2 | 5/2008 | Van De Velde |
| 7,510,282 | B2 | 3/2009 | Ueno |
| 7,520,613 | B2 | 4/2009 | Saito et al. |
| 7,703,922 | B2 | 4/2010 | Van De Velde |
| 8,480,659 | B2 | 7/2013 | Frey et al. |
| 8,652,602 | B1 | 2/2014 | Dolla |
| 8,783,868 | B2 | 7/2014 | Qiu |
| 8,876,808 | B2 | 11/2014 | Feklistov et al. |
| 8,994,753 | B2 | 3/2015 | Nakano |
| 9,033,500 | B2 | 5/2015 | Utsunomiya |
| 9,603,519 | B2 | 3/2017 | Bor et al. |
| 9,675,243 | B2 | 6/2017 | Sasak et al. |
| 9,789,002 | B2 | 10/2017 | Van De Velde |
| 10,130,511 | B2 | 11/2018 | Dantus |
| 10,478,342 | B2 | 11/2019 | Dick |
| 10,555,835 | B2 | 2/2020 | Schuele et al. |
| 2007/0258094 | A1 | 11/2007 | Izatt et al. |
| 2007/0291277 | A1 | 12/2007 | Everett |
| 2009/0073384 | A1 | 3/2009 | Warden |
| 2009/0137989 | A1 | 5/2009 | Kataoka |
| 2009/0196477 | A1 | 8/2009 | Cense et al. |
| 2010/0123873 | A1 | 5/2010 | Raymond |
| 2010/0152847 | A1 | 6/2010 | Padrick |
| 2011/0077557 | A1 | 3/2011 | Wing et al. |
| 2012/0281235 | A1 | 11/2012 | Murata |
| 2013/0131652 | A1 | 5/2013 | Dick |
| 2013/0173029 | A1 | 7/2013 | Caldeira et al. |
| 2014/0058367 | A1 | 2/2014 | Dantus |
| 2014/0216468 | A1 | 8/2014 | Goldshleger |
| 2014/0257257 | A1 | 9/2014 | Grant et al. |
| 2014/0268036 | A1 | 9/2014 | Ketterling et al. |
| 2014/0276674 | A1 | 9/2014 | Lee |
| 2015/0190278 | A1 | 7/2015 | Gooding |
| 2015/0342782 | A1 | 12/2015 | Mordaunt |
| 2016/0058617 | A1 | 3/2016 | Luttrull et al. |
| 2016/0074214 | A1 | 3/2016 | Palanker et al. |
| 2016/0074221 | A1 | 3/2016 | Tassignon et al. |
| 2016/0166431 | A1 | 6/2016 | Vogler et al. |
| 2016/0227999 | A1 | 8/2016 | An et al. |
| 2016/0235588 | A1 | 8/2016 | Hart et al. |
| 2016/0256324 | A1 | 9/2016 | Suzuki |
| 2016/0278629 | A1 | 9/2016 | Schuele |
| 2016/0302969 | A1 | 10/2016 | Yamamoto |
| 2017/0181625 | A1 | 6/2017 | Kawakami et al. |
| 2017/0252213 | A1 | 9/2017 | Furuuchi et al. |
| 2017/0326003 | A1 | 11/2017 | Schuele et al. |
| 2018/0028354 | A1 | 2/2018 | Heeren |
| 2018/0028355 | A1 | 2/2018 | Raksi |
| 2018/0140257 | A1 | 5/2018 | Govindjee et al. |
| 2018/0206719 | A1 | 7/2018 | Adler et al. |
| 2018/0317767 | A1 | 11/2018 | Ryan |
| 2018/0353064 | A1 | 12/2018 | Soetikno et al. |
| 2018/0368915 | A1 | 12/2018 | Xia et al. |
| 2019/0159933 | A1 | 5/2019 | Romano et al. |
| 2019/0282403 | A1 | 9/2019 | Barrett et al. |
| 2019/0290124 | A1 | 9/2019 | Laforest et al. |
| 2019/0313903 | A1 | 10/2019 | Mckinnon |
| 2019/0365569 | A1 | 12/2019 | Skovgaard et al. |
| 2020/0038241 | A1 | 2/2020 | Wang et al. |
| 2020/0060873 | A1 | 2/2020 | Heeren |
| 2020/0085292 | A1 | 3/2020 | Fukuma et al. |
| 2020/0129336 | A1 | 4/2020 | Schuele et al. |
| 2020/0130103 | A1 | 4/2020 | Choi |
| 2020/0192080 | A1 | 6/2020 | Karam |
| 2020/0196853 | A1 | 6/2020 | Van Hemert et al. |
| 2020/0273218 | A1 | 8/2020 | Camino et al. |
| 2020/0397289 | A1 | 12/2020 | Ralston |
| 2020/0400422 | A1 | 12/2020 | Ralston |
| 2021/0100450 | A1 | 4/2021 | Amma |
| 2021/0186753 | A1 | 6/2021 | Al-Qaisi et al. |
| 2021/0275009 | A1 | 9/2021 | Yates |
| 2021/0378507 | A1 | 12/2021 | Wallace |
| 2021/0386586 | A1 | 12/2021 | Bor |
| 2022/0012459 | A1 | 1/2022 | Schwiegerling |
| 2022/0031511 | A1 | 2/2022 | Charles |
| 2023/0157889 | A1 | 5/2023 | Bor |

FOREIGN PATENT DOCUMENTS

| | | |
|---|---|---|
| CN | 108371542 B | 4/2020 |
| CN | 109196333 B | 12/2020 |
| CN | 111281651 B | 12/2020 |
| CN | 112862782 A | 5/2021 |
| CN | 112587302 B | 6/2021 |
| CN | 112587304 B | 6/2021 |
| DE | 19705044 A1 | 8/1998 |
| DE | 102019007147 A1 | 4/2021 |
| DE | 102019007148 A1 | 4/2021 |
| EP | 0770370 A2 | 2/1997 |
| EP | 1212022 B1 | 3/2005 |
| EP | 1563785 A1 | 8/2005 |
| EP | 1638452 B1 | 10/2006 |
| EP | 1838212 A1 | 10/2007 |
| EP | 2144552 A1 | 1/2010 |
| EP | 1928297 B1 | 11/2010 |
| EP | 2459138 A2 | 6/2012 |
| EP | 2525706 A2 | 11/2012 |
| EP | 2898820 A1 | 7/2015 |
| EP | 3061429 A1 | 8/2016 |
| EP | 2890340 B1 | 2/2017 |
| EP | 3459487 A1 | 3/2019 |
| EP | 3501463 A1 | 6/2019 |
| EP | 3636137 A1 | 4/2020 |
| EP | 3861924 A1 | 8/2021 |
| GB | 2469249 A | 10/2010 |
| JP | 5767014 B2 | 6/2015 |
| JP | 2017176558 A | 10/2017 |
| JP | 6410468 B2 | 10/2018 |
| JP | 2018196821 A | 12/2018 |
| JP | 2018196822 A | 12/2018 |
| JP | 2020022569 A | 2/2020 |
| JP | 6736304 B2 | 7/2020 |
| JP | 6839902 B2 | 2/2021 |
| RU | 2661016 C1 | 7/2018 |
| RU | 2692666 C1 | 6/2019 |
| RU | 2695629 C1 | 7/2019 |
| RU | 2710058 C2 | 12/2019 |
| RU | 2726468 C1 | 7/2020 |
| WO | 9958047 A1 | 11/1999 |
| WO | 0137769 A1 | 5/2001 |
| WO | 0195791 A1 | 12/2001 |
| WO | 2007059189 A2 | 5/2007 |
| WO | 2009033110 A2 | 3/2009 |
| WO | 2009036104 A2 | 3/2009 |
| WO | 2009039315 A2 | 3/2009 |
| WO | 2009059400 A1 | 5/2009 |
| WO | 2010117386 A1 | 10/2010 |
| WO | 2014053824 A1 | 4/2014 |

(56) References Cited

FOREIGN PATENT DOCUMENTS

| | | |
|---|---|---|
| WO | 2015131135 A1 | 9/2015 |
| WO | 2015171793 A1 | 11/2015 |
| WO | 2016033590 A1 | 3/2016 |
| WO | 2017062673 A1 | 4/2017 |
| WO | 2017196306 A1 | 11/2017 |
| WO | 2017205857 A1 | 11/2017 |
| WO | 2020074532 A1 | 4/2020 |
| WO | 2020180729 A1 | 9/2020 |
| WO | 2020215359 A1 | 10/2020 |
| WO | 2020216763 A1 | 10/2020 |
| WO | 2020257711 A1 | 12/2020 |
| WO | 2021023799 A1 | 2/2021 |
| WO | 2021049243 A1 | 3/2021 |
| WO | 2021066047 A1 | 4/2021 |
| WO | 2021092211 A1 | 5/2021 |
| WO | 2021183637 A1 | 9/2021 |
| WO | 2022149028 A1 | 7/2022 |
| WO | 2023089416 A1 | 5/2023 |
| WO | 2023089459 A1 | 5/2023 |
| WO | 2023097391 A1 | 6/2023 |

OTHER PUBLICATIONS

Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.

Ginner et al., "Wide-Field OCT Angiography at 400 KHz Utilizing Spectral Splitting", Photonics, Oct. 23, 2014, pp. 369-379, vol. 1, No. 4.

Heidelberg Engineering GMBH, "Spectralis. Hardware Operating Instructions," Version 001, Aug. 2007.

Heidelberg Engineering, "Spectralis. Multimodal Imaging Platform Optimized for the Posterior Segment", accessed on Jan. 30, 2023 from https://business-lounge.heidelbergengineering.com/us/en/products/spectralis/spectralis/.

Hofer et al., "Dispersion encoded full range frequency domain optical coherence tomography", Jan. 5, 2009, pp. 7-24, vol. 17, No. 1, Optics Express, US.

Hofer et al., "Fast dispersion encoded full range optical coherence tomography for retinal imaging at 800 nm and 1060 nm", Mar. 1, 2010, pp. 4898-4919, vol. 18, No. 5, Optics Express.

Leitgeb et al., "Complex ambiguity-free Fourier domain optical coherence tomography through transverse scanning", 2007, pp. 3453-3455, vol. 32, Optics Letters.

Li et al., "DMD-based three-dimensional chromatic confocal microscopy", 2020, pp. 4349-4356, vol. 59, No. 14, Applied Optics.

Martial et al., "Programmable Illumination and High-Speed, Multi-Wavelength, Confocal Microscopy Using a Digital Micromirror", Aug. 2012, e43942, vol. 7, No. 8, PLOS One.

Reznicek Lukas et al., "Wide-Field Megahertz OCT Imaging of Patients with Diabetic Retinopathy", Journal of Diabetes Research, 2015, 5 pages.

Ruggeri et al., "Imaging and full-length biometry of the eye during accommodation using spectral domain OCT with an optical switch", Jul. 1, 2012, pp. 1506-1520, vol. 3, No. 7, Biomedical Optics Express.

Sarunic et al., "Instantaneous complex conjugate resolved spectral domain and swept-source OCT using 3x3 fiber couplers", Feb. 2005, pp. 957-967, vol. 13, No. 3, Optics Express.

Shields et al., "Wide-angle Imaging of the Ocular Fundus", Review of the Ophthalmology, Feb. 15, 2003.

Singh, "Lasers Take Aim at Floaters", Ophthalmology Management, Jul. 1, 2019, pp. 38, 40-42, 59, vol. 23.

Singh, "Modern vitreolysis—YAG laser treatment now a real solution for the treatment of symptomatic floaters", Survey of Ophthalmology, Mar. 3, 2020, pp. 581-591, vol. 65, No. 5.

SunLED, NanoPoint-0201 Series LEDs, published Feb. 15, 2016, www.SunLEDusa.com.

Volk Optical, "Volk Idrees Mid-Vitreous Lens", Dec. 20, 2020, accessed on Dec. 20, 2020 from https://www.volk.com/...s?pr_prod_strat=collection_fallback&pr_rec_pid=4513049018402&pr_ref_pid=4513048952866&pr_seq=uniform.

Wang et al., "In vivo full range complex Fourier domain optical coherence tomography", Jan. 30, 2007, 054103, vol. 90, Applied Physics Letters.

Wojtkowski et al., "Full range complex spectral optical coherence tomography technique in eye imaging", 2002, pp. 1415-1417, vol. 27, No. 16, Optics Letters.

Yasuno et al., "Simultaneous B—M-mode scanning method for real-time full-range Fourier domain optical coherence tomography", 2006, pp. 1861-1865, vol. 45, No. 8, Applied Optics.

Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.

Zhou et al., "Dual channel dual focus optical coherence tomography for imaging accommodation of the eye", May 25, 2009, pp. 8947-8955, vol. 17, No. 11, Optics Express.

Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.

Chirag P. Shah, et al., YAG Laser Vitreolysis vs Sham YAG Vitreolysis for Symptomatic Vitreous Floaters a Randomized Clinical Trial, JAMA Ophthalmology, Sep. 2017, 918-923, 135-9.

Ellex Website, Treatment Guidelines—Laser Floater Removal; 2016, Ellex Medical Pty Ltd. E&OE. VB0002E, downloaded Apr. 20, 2017.

Felix Sauvage et al: "Photoablation of Human Vitreous Opacities by Light—Induced Vapor Nanobubbles", ACS Nano, vol. 13, No. 7, Jul. 9, 2019, pp. 8401-8416.

Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.

Michael J. Escuti, et al., "Geometric-Phase Holograms", Optics & Photonics News, pp. 22-29, Feb. 2016.

Milston Rebecca et al: "Vitreous floaters: Etiology, diagnostics, and management", Survey of Ophthalmology, vol. 61, No. 2, Mar. 1, 2016, pp. 211-227.

Nicusor Iftimia et al: "Hybrid retinal imaginer using line-scanning laser ophthalmoscopy and spectral domain optical coherence tomography", Optics Express, vol. 14, No. 26, Dec. 22, 2006.

Reece Bergstrom, et al., Vitreous Floaters, National Center for Biotechnology Information, May 21, 2020, 4 pages, Bookshelf ID NBK470420, StatPearls Publishing LLC, online.

Wikipedia Encyclopedia, Floater, Wikipedia Encyclopedia, Mar. 29, 2021, online: https://en.wikipedia.org/wiki/rloater?wprov=sfti 1.

Zhang Yunbo et al: "Parallel large-range scanning confocal microscope based on a digital micromirror device", Optik vol. 124, No. 13 (2013), Aug. 4, 2012, pp. 1585-1588.

Adrian G.H. Podoleanu et al., Combined optical coherence tomograph and scanning laser ophthalmoscope mi nije dostupan besplatno., Electronics Letters, 34 (11), 1998.

Chi-Hung Lee, et al., Imaging vitreous floaters and cataracts with optical simulations, Optik, 194, 1-9, 2019.

Christy K. Sheehy et al., High-speed, image-based eye tracking with a scanning laser ophthalmoscope, Biomedical Optics Express, vol. 3, No. 10, 2012.

D. H. Kelly, "Retinal Inhomogeneity. II. Spatial Summation," J. Opt. Soc. Am., pp. 114-119, vol. 1, No. 1 (Jan. 1984).

D. H. Kelly, "Retinal Inhomogeneity. III. Circular-Retina Theory," D.H. Kelly, J. Opt. Soc. Am., pp. 810-819, vol. 2, No. 6 (Jun. 1985).

D.H. Kelly, "Visual Processing of Moving Stimuli," J. Opt. Soc. Am., pp. 216-225, vol. 2, No. 2 (Feb. 1985).

D.H. Kelly,, "Motion and Vision. II. Stabilized Spatio-Temporal Threshold Surface," J. Opt. Soc. Am., pp. 1340-1349, vol. 69, No. 10 (Oct. 1979).

(56) References Cited

OTHER PUBLICATIONS

D.H.Kelly, "Retinal Inhomogeneity. I. Spatiotemporal Contrast Sensitivity," J. Opt. Sec. Am., pp. 107-113, vol. 1, No. 1 (Jan. 1984).
Mojana F. et al.. Observations by spectral-domain optical coherence tomography combined with simultaneous scanning laser ophthalmoscopy: imaging of the vitreous, American Journal of Ophthalmol. Apr. 2010;149(4):641-650.
Nidek, Scanning Laser Ophthalmoscope Mirante SLO/OCT Mirante SLO, https://www.nidek-intl.com/product/ophthaloptom/diagnostic/dia_retina/mirante.htm.
Peter G. J. Barten, "Contrast Sensitivity of the Human Eye and its Effects on Image Quality," Chapter 3, pp. 27-40, Model for the spatial contrast sensitivity of the eye, (1999).
Pointer, J. S., & Hess, R. F. "The contrast sensitivity gradient across the human visual field: With emphasis on the low spatial frequency range,", R. F. Vision Research, 29(9), 1133-1151 (1989).
Sebag J et al., Vitreous and Vitreoretinal Interface, Ch. 21, 2015.
Sebag J., Vitreous and Vision Degrading Myodesopsia. Progress in Retinal and Eye Research Nov. 2020;79.
T Ivanova et al., Vitrectomy for primary symptomatic vitreous opacities: an evidence-based review, Eye (Lond) May 2016;30(5):645-55.
Teri T Kleinberg et al., Vitreous substitutes: a comprehensive review, Survey of Ophthalmology, 56 (4), 2011.
Volk Optical, "Volk Singh Mid-Vitreous Lens", Dec. 20, 2020, accessed on Dec. 20, 2020 from https://www.volk.com/products/singh-mid-vitreous-vitreous-slit-lamp-lens?_pos+3&_sid=b50c0674f&_ss=r.

GENERATING AND EVALUATING TWO- AND THREE-DIMENSIONAL IMAGES OF THE INTERIOR OF AN EYE

TECHNICAL FIELD

The present disclosure relates generally to ophthalmic surgical systems, and more particularly to generating and evaluating two- and three-dimensional images of the interior of an eye.

BACKGROUND

Laser vitreolysis uses laser beams to treat vitreous floaters and other retinal diseases. Precise delivery of a laser beam to the target is important to avoid damaging healthy tissue and ensure ocular safety. Accordingly, imaging systems should provide sufficiently clear images of targets. However, known imaging systems are not satisfactory in certain situations.

BRIEF SUMMARY

In certain embodiments, an ophthalmic laser surgical system for imaging and treating a target in an eye includes an optical coherence tomography (OCT) device, a laser device, an xy-scanner, and a computer. The eye has an eye axis that defines a z-axis, which defines xy-planes within the eye. The OCT device directs an imaging beam along an imaging beam path towards the eye; receives the imaging beam reflected from the eye; generates three-dimensional (3D) image data from the reflected imaging beam; and generates two-dimensional (2D) enface images from the 3D image data. A 2D enface image images an xy-plane within the eye. The 2D enface images include a target enface image imaging the target in the eye and a retinal enface image imaging a retina of the eye. The retinal enface image shows a shadow cast by the target onto the retina. The laser device directs a laser beam along a laser beam path towards the target. The xy-scanner receives the imaging beam from the imaging system and directs the imaging beam along the imaging beam path towards the eye; and receives the laser beam from the laser device and directs the laser beam along the laser beam path aligned with the imaging beam path towards the eye. The computer compares the target of the target enface image and the shadow of the retinal enface image to confirm the presence of the target.

Embodiments may include none, one, some, or all of the following features:

The target comprises a vitreous eye floater.
The OCT device generates the two-dimensional (2D) enface images from the 3D image data by: taking a slice of the 3D image data; and summing data of the slice to yield a 2D enface image.
The OCT device generates the two-dimensional (2D) enface images from the 3D image data by: taking a slice of the 3D image data; and averaging data of the slice to yield a 2D enface image.
The OCT device generates the two-dimensional (2D) enface images from the 3D image data by: taking a slice of the 3D image data; and projecting data of the slice to yield a 2D enface image.
The computer performs image processing on the target enface image to determine a feature of the target. The computer may perform image processing on the target enface image to identify an outline of the target, and determine a size of the target from the outline of the target. The computer may perform image processing on the target enface image to identify an outline of the target, and determine a shape of the target from the outline of the target.
The computer tracks the target according to the target enface image imaging the target.
The computer tracks the target by tracking the shadow cast by the target according to the retinal enface image.
The computer overlays an outline of the target onto the target enface image.
The computer overlays a no-fire zone onto the target enface image.
The OCT device generates three-dimensional (3D) images from the 3D image data.

In certain embodiments, a method images and treats a target in an eye. The eye has an eye axis that defines a z-axis, which defines xy-planes within the eye. The method includes: directing, by an optical coherence tomography (OCT) device, an imaging beam along an imaging beam path towards the eye; receiving the imaging beam reflected from the eye; generating three-dimensional (3D) image data from the reflected imaging beam; and generating two-dimensional (2D) enface images from the 3D image data. A 2D enface image images an xy-plane within the eye. The 2D enface images include a target enface image imaging the target in the eye and a retinal enface image imaging a retina of the eye. The retinal enface image shows a shadow cast by the target onto the retina. The method further includes: directing, by a laser device, a laser beam along a laser beam path towards the target; receiving, by an xy-scanner, the imaging beam from the imaging system and direct the imaging beam along the imaging beam path towards the eye; receiving, by the xy-scanner, the laser beam from the laser device and direct the laser beam along the laser beam path aligned with the imaging beam path towards the eye; and comparing, by a computer, the target of the target enface image and the shadow of the retinal enface image to confirm the presence of the target.

Embodiments may include none, one, some, or all of the following features:

The generating the two-dimensional (2D) enface images from the 3D image data includes: taking a slice of the 3D image data; and summing, averaging, or projecting data of the slice to yield a 2D enface image.
The method further includes performing, by the computer, image processing on the target enface image to determine a feature of the target. The computer may perform image processing on the target enface image to identify an outline of the target, and determine a size of the target from the outline of the target. The computer may perform image processing on the target enface image to identify an outline of the target, and determine a shape of the target from the outline of the target.
The method further includes tracking, by the computer, the target according to the target enface image imaging the target.
The method further includes tracking, by the computer, the target by tracking the shadow cast by the target according to the retinal enface image.
The method further includes overlaying, by the computer, an outline of the target or a no-fire zone onto the target enface image.
The method further includes generating, by the OCT device, a plurality of three-dimensional (3D) images from the 3D image data.

In certain embodiments, an ophthalmic laser surgical system for imaging and treating a target in an eye includes an optical coherence tomography (OCT) device, a laser device, an xy-scanner, and a computer. The eye has an eye axis that defines a z-axis, which defines xy-planes within the eye. The target is a vitreous eye floater. The OCT device directs an imaging beam along an imaging beam path towards the eye; receives the imaging beam reflected from the eye; generates three-dimensional (3D) image data from the reflected imaging beam; and generates two-dimensional (2D) enface images from the 3D image data. The OCT device generates the 2D enface images from the 3D image data by taking a slice of the 3D image data and summing, averaging, or projecting data of the slice to yield a 2D enface image. A 2D enface image images an xy-plane within the eye. The 2D enface images include a target enface image imaging the target in the eye and a retinal enface image imaging a retina of the eye. The retinal enface image shows a shadow cast by the target onto the retina. The laser device directs a laser beam along a laser beam path towards the target. The xy-scanner receives the imaging beam from the imaging system and directs the imaging beam along the imaging beam path towards the eye; and receives the laser beam from the laser device and directs the laser beam along the laser beam path aligned with the imaging beam path towards the eye. The computer performs the following: compares the target of the target enface image and the shadow of the retinal enface image to confirm the presence of the target; performs image processing on the target enface image to determine a feature of the target by performing image processing on the target enface image to identify an outline of the target and determining a size of the target from the outline of the target, and by performing image processing on the target enface image to identify an outline of the target and determining a shape of the target from the outline of the target; tracks the target according to the target enface image imaging the target; tracks the target by tracking the shadow cast by the target according to the retinal enface image; overlays an outline of the target onto the target enface image; overlays a no-fire zone onto the target enface image; and generates a plurality of three-dimensional (3D) images from the 3D image data.

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Known surgical systems include imaging systems, such as scanning laser ophthalmoscope (SLO) and optical coherence tomography (OCT) devices, to provides images of targets or their shadows. An SLO device provides two-dimensional (2D) enface images of a target or its shadow on the retina, and an OCT device provides three-dimensional (3D) images of the target. However, these known surgical systems have disadvantages. The two different imaging technologies, SLO and OCT, add expense and complexity to the system. In addition, the known surgical systems make it difficult to determine whether the image shows a target shadow or, e.g., a lens opacity, vignetting, retinal pathology, or imaging artifact.

Accordingly, embodiments of the surgical systems described herein include an OCT device that gathers 3D OCT data and generates both 3D images and 2D enface images from the data. A 2D enface image can be generated from a "slice" of the 3D OCT data between two surfaces, e.g., two xy-planes or layers of the tissue of the eye. A spatial mapping of features between the surfaces yields a 2D enface image.

Certain embodiments may offer several advantages. The surgical systems can use the 2D enface images to determine the presence, size, shape, and/or location of the target. For example, a 2D image of the target can be compared with a 2D image of its shadow to confirm the presence of the target. As another advantage, the surgical systems use only one device (the OCT device) instead of two devices (the OCT and SLO devices) to provide 3D images and 2D enface images, which reduces the cost and complexity of certain embodiments.

As yet another advantage, the surgical systems co-register the OCT and laser devices such that the laser beam can be precisely directed to the target using a 2D enface image. The OCT and laser devices share a beam path through the same optical elements, including an xy-scanner, and through the eye. If the OCT and laser beams are aligned prior to the shared optical elements, the beams are automatically aligned at the target location in the eye, allowing for precise image-guided beam targeting.

Figure 1:
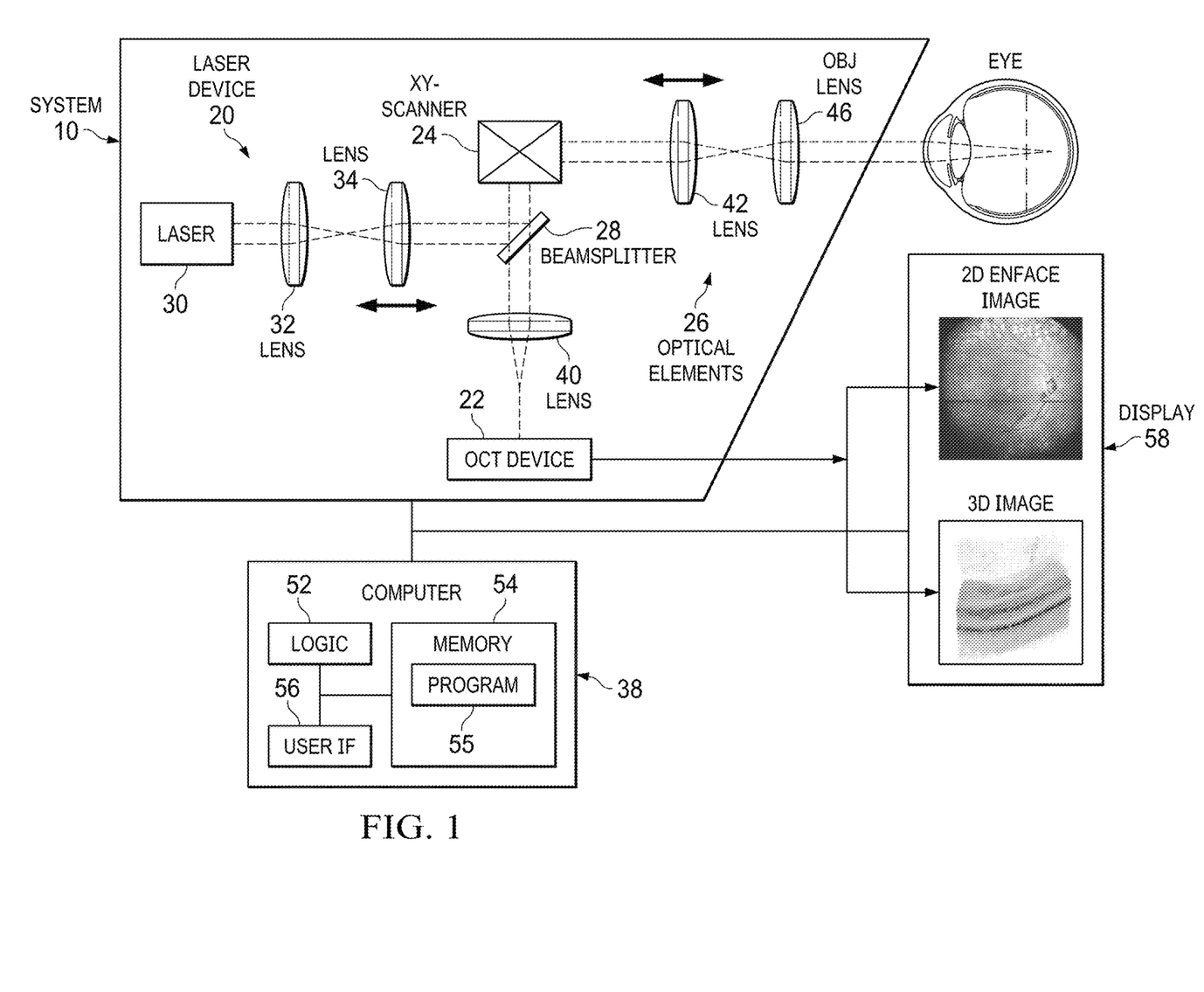
FIG. 1 illustrates an example of an ophthalmic surgical system that can image and treat a target in an eye, according to certain embodiments.

FIG. 1 illustrates an example of an ophthalmic surgical system 10 that can image and treat a target in an eye, according to certain embodiments. In the example, the target is a vitreous eye floater in the vitreous of the eye. In the example, an axis of the eye (e.g., visual or optical) defines a z-axis, which in turn define x- and y-axes orthogonal to the z-axis. X- and y-axes define xy-planes within the eye. X-, y-, and z-directions and locations are relative to the x-, y-, and z-axes, respectively.

In the example, system 10 includes a treatment system (which comprises a laser device 20), an imaging system (which comprises an optical coherence tomography (OCT) device 22), an xy-scanner 24, optical elements 26, and a computer 38, coupled as shown. Laser device 20 includes a laser 30 and lenses 32, 24, coupled as shown. Optical elements includes beamsplitter (e.g., a dichroic mirror (DM)) 28 and lenses 32, 34, 40, 42, and 46, coupled as shown. Computer 38 includes logic 52, memory 54 (which stores a computer program 55), a user interface (IF) 56, and a display 58, coupled as shown.

As an example of operation, OCT device 22 directs an imaging beam along an imaging beam path towards the eye, receives the imaging beam reflected from the eye, generates three-dimensional (3D) image data from the reflected imaging beam, and generates two-dimensional (2D) enface images from the 3D image data. A 2D enface image images an xy-plane within the eye. For example, a target enface image images a target in the eye. Laser device 20 directs a laser beam along a laser beam path towards the target. OCT device 22 and laser device 20 share the same xy-scanner 24, which allows for precise aiming of the laser beam using the imaging. That is, xy-scanner 24 receives the imaging beam from the imaging system and directs the imaging beam along the imaging beam path towards the target, and receives the laser beam from the laser device and directs the laser beam along the laser beam path aligned with the imaging beam path towards the target. In certain embodiments, OCT device 22 combines 2D enface images to generate a three-dimensional (3D) image, where the 3D image images a volume within the eye.

Turning to the treatment system, laser 30 of laser device 22 generates a laser beam with any suitable wavelength, e.g., in a range from 400 nm to 2000 nm. Laser device 22 delivers laser pulses at any suitable repetition rates ranging from, but not limited to, 1 hertz (Hz) to several hundreds of kilohertz (kHz). A laser pulse may have any suitable pulse duration (e.g., ranging from, but not limited to, a nanosecond (ns) to 20 femtoseconds (fs)), any suitable pulse energy (e.g., 1 microjoule (µJ) to 10 millijoule (mJ)), and a focal point of any suitable size (e.g., ranging from 3 to 20 microns (µm), such as 7 µm). Lenses 32 and 34 are used to adjust the focus position of the laser beam within tissue, such as eye tissue.

Turning to the imaging system, OCT device 22 generates 3D images and 2D enface images of the interior of the eye from the imaging beam reflected from the eye. A 2D enface image may be regarded as a pseudo-SLO image, as OCT device 22 can generate 2D enface images that are very similar to SLO images. OCT device 22 may be any suitable device that utilizes optical coherence tomography to generate images, e.g., a swept-source OCT (SS-OCT), line-field OCT, full-field OCT, or spectral-domain OCT (SD-OCT) device.

In certain embodiments, OCT device 22 generates the 2D and 3D images from 3D image data determined from the reflected imaging beam. OCT device 22 performs a series of A-scans (i.e., scans in the z-direction), combines the A-scans to form B-scans, and combines the B-scans to yield 3D image data, which can be used to generate a 3D image. To generate a 2D enface image, OCT device 22 takes a slice of the 3D image data that is generally orthogonal to the z-axis. The slice is bounded by two non-intersecting surfaces. The surfaces may represent, e.g., xy-planes or layers of eye tissue. The data in the slice is processed (e.g., averaged, summed, projected) to yield a 2D enface image. For example, for each point (x, y), the values of the image data at point (x, y) are averaged (or summed, projected, or otherwise processed) to yield the value for point (x, y) of the enface image.

In other embodiments, OCT device 22 generates the 2D enface images directly from the A-scans. OCT device 22 generates an A-scan, which a value for an xy-point of an xy-plane. Multiple A-scans yield values for multiple points of an xy-plane, which can be used to generate a 2D enface image at the xy-plane.

Xy-scanner 36 scans treatment and imaging beams transversely in xy-directions. Examples of scanners include a galvo scanner (e.g., a pair of galvanometrically-actuated scanner mirrors that can be tilted about mutually perpendicular axes), an electro-optical scanner (e.g., an electro-optical crystal scanner) that can electro-optically steer the beam, or an acousto-optical scanner (e.g., an acousto-optical crystal scanner) that can acousto-optically steer the beam.

OCT device 22 and laser device 20 share xy-scanner 24, allowing for co-registration between the OCT imaging and treatment beams. That is, xy-scanner 24 receives the imaging beam from the imaging system and directs the imaging beam along the imaging beam path towards the target, and receives the laser beam from the laser device and directs the laser beam along the laser beam path co-aligned with the imaging beam path towards the target. The OCT imaging and treatment beams share the same path through the optics of the system and the eye, so are affected by the same optical properties and distortions along the beam path. Thus, if the imaging and treatment beams are aligned prior to xy-scanner 24, they are automatically aligned at the target location. This enables accurate and precise delivery of the laser beam to the target location identified using OCT images.

Optical elements includes beamsplitter (such as a dichroic mirror (DM)) 28 and lenses 32, 34, 40, 42, and 46, coupled as shown. In general, an optical element can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, lens 40 collimates beams to and from beamsplitter 28. Beamsplitter 28 directs beams from OCT device 22 and laser device 20 to xy-scanner 24 and directs beam reflected from the eye back to OCT device 22. Beamsplitter 28 may comprise any suitable beam splitter that can combine beams or separate one beam into multiple beams. For example, a dichroic mirror can combine or split beams of different wavelengths, depending on the configuration. Lenses 32 and 34 collimates the beam from laser 30. Lens 42 and objective lens 46 collimate and focus beams at the eye.

Computer 38 sends instructions to the OCT device and the laser device. Computer 38 may utilize computer programs 55 to perform operations. Examples of computer programs 55 include target imaging, target tracking, image processing, and target evaluation.

In certain embodiments, computer 26 uses an image processing program 55 to perform image processing on an image, e.g., analyze the digital information of the image to extract information from the image. In certain embodiments, computer 26 performs image processing to analyze an image of a target or a target's shadow (i.e., "target shadow") to obtain information about the target. Localized opacities in the vitreous, such as floaters, can affect vision quality when they are in the path of light and cast a shadow onto the retina. Hence, the target shadow can provide useful information about clinical significance of the floater or other opacity. Moreover, target shadows may yield higher contrast, clearer images than the targets themselves. Accordingly, images of a target shadow may be easier to analyze to evaluate, e.g., the location, size, or density of the target. In addition, it may be easier to track the target shadow to determine the location of the target.

In the embodiments, computer 26 may analyze the target and/or target shadow in any suitable manner. For example, computer 26 may detect a brighter or darker shape in an image (using, e.g., edge detection or pixel analysis) to detect the target or the target shadow. As another example, program 54 may identify an outline of the target, and determine a size and/or shape of the target from the outline. As another example, program 54 may detect the darkness of the target shadow, i.e., how dark the shadow is. In general, a thicker and/or denser target may yield a darker shadow. Similarly, a target closer to the retina may yield a darker shadow. Accordingly, program 54 may analyze the target and/or target shadow to determine clinically relevant information about the target.

In certain embodiments, computer 38 performs image processing to confirm the presence of the target. OCT device 22 generates a target enface image that shows a target candidate and a retinal enface image that shows a shadow. Computer 38 compares the target candidate and the shadow to confirm the presence of the target. For example, computer 38 may align the images to determine that the target casts the shadow. This may rule out shadows caused by, e.g., a lens opacity, vignetting, retinal pathology, or other imaging artifacts. In certain embodiments, computer 38 performs image processing to generate 2D and 3D images, as described above.

In certain embodiments, computer 38 uses a tracking program to track and/or predict the movement of a target. In some situations, the enface image of the target itself may be clearer than the image of the shadow of the target, so computer 38 may track the target using the target enface image rather than the retinal enface image with the target shadow. In other situations, the retinal enface image with the target shadow may be more appropriate, so computer 38 may track the target using the target shadow. The tracking program may predict the movement of the target and send to laser device 20 the location of where the target is predicted to be when the laser beam reaches the target. The images of the target may be used to acquire the target (e.g., determine the fingerprint of a floater) and fire the laser beam at the target.

In certain embodiments, computer 38 generates image overlays to superimpose over images of the eye. Examples of image overlays include an outline of the target, a no-fire zone indicating where the laser should not be fired (such as the foveal region), information describing the target (e.g., target size, shape, and/or density) or the eye, or other suitable overlay that enhances the image. Examples of eye images over which an image overlay may be superimposed include a retinal enface image, target enface image, real time video of the eye, or other suitable image of the eye. For example, computer 38 may superimpose an outline of the target onto a retinal enface image, a no-fire zone onto a target enface image, or the target size, shape, and/or density onto a real time video of the eye.

Figure 2A:
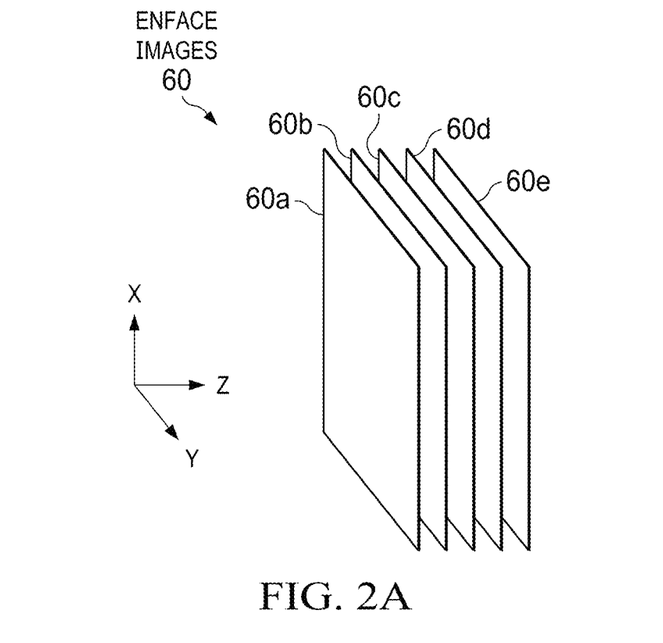
FIGS. 2A and 2B illustrate examples of two-dimensional (2D) enface images that may be generated by the OCT device of the system of FIG. 1.
Figure 2B:
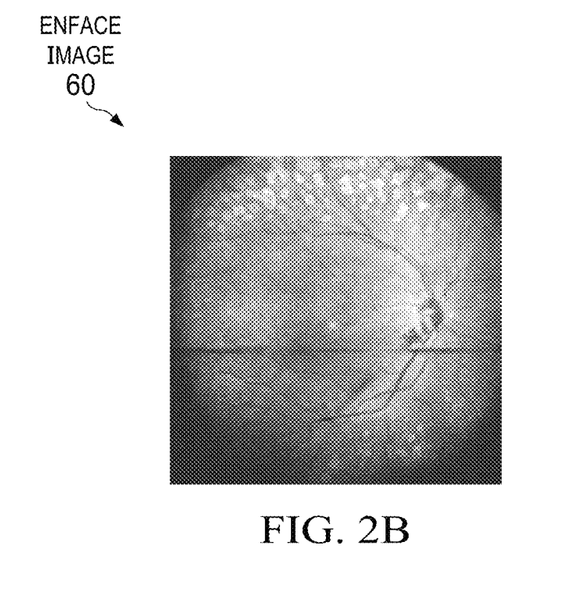

FIGS. 2A and 2B illustrate examples of two-dimensional (2D) enface images 60 that may be generated by OCT device 22 of system 10 of FIG. 1. FIG. 2A shows examples of enface images 60 (60a to 60e). In the examples, each image is located at an xy-plane within the eye, and each xy-plane is located at a different z-location. Enface images 60 include, e.g., a target enface image that images a target in the eye and a retinal enface image that images the retina of the eye. The retinal enface image may also show the shadow cast by the target onto the retina. FIG. 2B shows an example of an enface image 60 generated at the retina of the eye.

Figure 3:
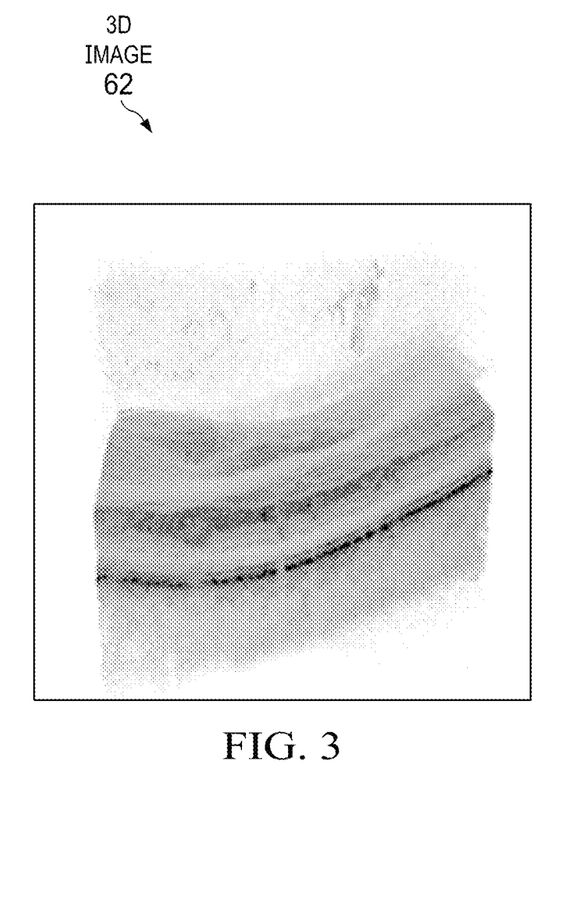
FIG. 3 illustrates an example of a three-dimensional (3D) image that may be generated by the OCT device of the system of FIG. 1.

FIG. 3 illustrates an example of a three-dimensional (3D) image 62 that may be generated by OCT device 22 of system 10 of FIG. 1 from 3D OCT image data. In the example, 3D image 62 images a volume within the eye. The volume image may show the target and/or retina.

Figure 4:
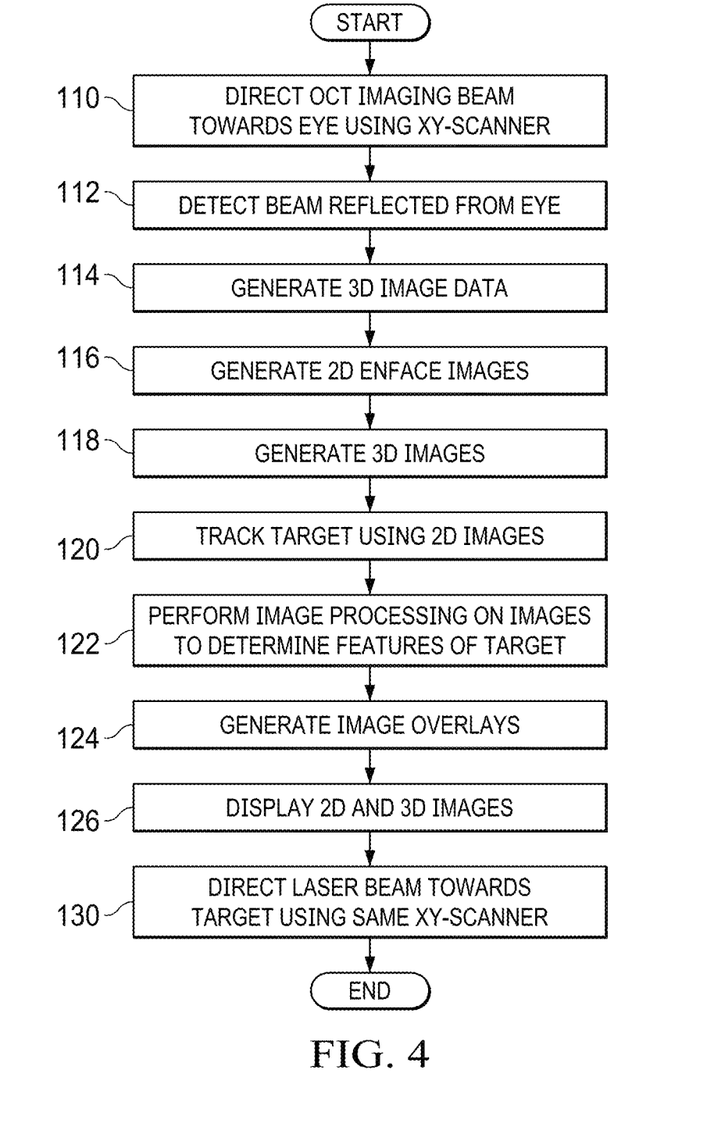
FIG. 4 illustrates an example of a method for imaging and treating a target in the vitreous of an eye, according to certain embodiments.

FIG. 4 illustrates an example of a method for imaging and treating a target in the vitreous of an eye, according to certain embodiments. The method starts at step 110, where the OCT device directs an OCT imaging beam towards the eye via an xy-scanner. The OCT device detects the reflected OCT imaging beam at step 112. The OCT device generates 3D image data from the reflected beam at step 114. The image data is generated from multiple A-scans and B-scans.

The OCT device generates 2D enface images of the target from the 3D image data at step 116. Enface images include, e.g., a target enface image that images a target in the eye and a retinal enface image that images the retina of the eye. The retinal enface image may also show the shadow cast by the target onto the retina. The OCT device generates 3D images of the target at step 118. The 3D image 62 images a volume within the eye. A computer tracks the target using the 2D images at step 120. In the embodiments, the computer may use the enface image of the target or the target shadow to track the target.

The computer performs image processing of the images to determine features of the target at step 122. For example, the OCT device generates a target enface image that shows a target candidate and a retinal enface image that shows a shadow, and compares the target candidate and the shadow to confirm the presence of the target. As another example, a computer program may identify an outline of the target from the target enface image, and determine the size and/or shape of the target from the outline. As another example, a computer program may detect the darkness of the target shadow from the retinal enface image, and determine the density or thickness of the target from the darkness of the shadow.

The computer generates image overlays at step 124 to superimpose over images of the eye. For example, the computer may superimpose an outline of the target onto a retinal enface image, a no-fire zone onto a target enface image, or the target size, shape, and/or density onto a real time video of the eye. The computer displays the images at step 126. The laser device directs a laser beam towards the target via the same xy-scanner at step 130. OCT device 22 and laser device 20 share xy-scanner 24, allowing for co-registration between the imaging and treatment beams for more precise aiming of the laser beam. The method then ends.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD)

or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic laser surgical system for imaging and treating a target in an eye, comprising:
   an optical coherence tomography (OCT) device configured to:
   direct an imaging beam along an imaging beam path towards the eye, the eye having an eye axis, the eye axis defining a z-axis, the z-axis defining a plurality of xy-planes within the eye;
   receive the imaging beam reflected from the eye;
   generate three-dimensional (3D) image data from the reflected imaging beam; and
   generate a plurality of two-dimensional (2D) enface images from the 3D image data, a 2D enface image imaging an xy-plane within the eye, the plurality of 2D enface images comprising at least one target enface image imaging the target in the eye and a retinal enface image imaging a retina of the eye, the retinal enface image showing a shadow cast by the target onto the retina;
   a laser device configured to direct a laser beam along a laser beam path towards the target;
   an xy-scanner configured to:
   receive the imaging beam from the OCT device and direct the imaging beam along the imaging beam path towards the eye; and
   receive the laser beam from the laser device and direct the laser beam along the laser beam path aligned with the imaging beam path towards the eye; and
   a computer configured to:
   compare the target of the target enface image and the shadow of the retinal enface image to confirm the presence of the target.

2. The ophthalmic laser surgical system of claim 1, the target comprising a vitreous eye floater.

3. The ophthalmic laser surgical system of claim 1, the OCT device configured to generate the two-dimensional (2D) enface images from the 3D image data by:
   taking a slice of the 3D image data; and
   summing data of the slice to yield a 2D enface image.

4. The ophthalmic laser surgical system of claim 1, the OCT device configured to generate the two-dimensional (2D) enface images from the 3D image data by:
   taking a slice of the 3D image data; and
   averaging data of the slice to yield a 2D enface image.

5. The ophthalmic laser surgical system of claim 1, the OCT device configured to generate the two-dimensional (2D) enface images from the 3D image data by:
   taking a slice of the 3D image data; and
   projecting data of the slice to yield a 2D enface image.

6. The ophthalmic laser surgical system of claim 1, the computer configured to:
   perform image processing on the target enface image to determine a feature of the target.

7. The ophthalmic laser surgical system of claim 6, the computer configured to:
   perform image processing on the target enface image to identify an outline of the target; and
   determine a size of the target from the outline of the target.

8. The ophthalmic laser surgical system of claim 6, the computer configured to:
   perform image processing on the target enface image to identify an outline of the target; and
   determine a shape of the target from the outline of the target.

9. The ophthalmic laser surgical system of claim 1, the computer configured to:
   track the target according to the target enface image imaging the target.

10. The ophthalmic laser surgical system of claim 1, the computer configured to:
    track the target by tracking the shadow cast by the target according to the retinal enface image.

11. The ophthalmic laser surgical system of claim 1, the computer configured to:
    overlay an outline of the target onto the target enface image.

12. The ophthalmic laser surgical system of claim 1, the computer configured to:
    overlay a no-fire zone onto the target enface image.

13. The ophthalmic laser surgical system of claim 1, the OCT device configured to:
    generate a plurality of three-dimensional (3D) images from the 3D image data.

14. A method for imaging and treating a target in an eye, comprising:
    directing, by an optical coherence tomography (OCT) device, an imaging beam along an imaging beam path towards the eye, the eye having an eye axis, the eye axis defining a z-axis, the z-axis defining a plurality of xy-planes within the eye;
    receiving the imaging beam reflected from the eye;
    generating three-dimensional (3D) image data from the reflected imaging beam;
    generating a plurality of two-dimensional (2D) enface images from the 3D image data, a 2D enface image imaging an xy-plane within the eye, the plurality of 2D enface images comprising at least one target enface image imaging the target in the eye and a retinal enface image imaging a retina of the eye, the retinal enface image showing a shadow cast by the target onto the retina;

directing, by a laser device, a laser beam along a laser beam path towards the target;

receiving, by an xy-scanner, the imaging beam from the OCT device and direct the imaging beam along the imaging beam path towards the eye;

receiving, by the xy-scanner, the laser beam from the laser device and direct the laser beam along the laser beam path aligned with the imaging beam path towards the eye; and comparing, by a computer, the target of the target enface image and the shadow of the retinal enface image to confirm the presence of the target.

15. The method of claim 14, the generating the two-dimensional (2D) enface images from the 3D image data comprising:

taking a slice of the 3D image data; and summing, averaging, or projecting data of the slice to yield a 2D enface image.

16. The method of claim 14, further comprising:

performing, by the computer, image processing on the target enface image to determine a feature of the target.

17. The method of claim 16, the performing, by the computer, image processing on the target enface image to determine a feature of the target comprising:

performing image processing on the target enface image to identify an outline of the target; and determining a size of the target from the outline of the target.

18. The method of claim 16, the performing, by the computer, image processing on the target enface image to determine a feature of the target comprising:

performing image processing on the target enface image to identify an outline of the target; and determining a shape of the target from the outline of the target.

19. The method of claim 14, further comprising:

tracking, by the computer, the target according to the target enface image imaging the target.

20. The method of claim 14, further comprising:

tracking, by the computer, the target by tracking the shadow cast by the target according to the retinal enface image.

21. The method of claim 14, further comprising:

overlaying, by the computer, an outline of the target or a no-fire zone onto the target enface image.

22. The method of claim 14, further comprising:

generating, by the OCT device, a plurality of three-dimensional (3D) images from the 3D image data.

23. An ophthalmic laser surgical system for imaging and treating a target in an eye, comprising:

an optical coherence tomography (OCT) device configured to:

direct an imaging beam along an imaging beam path towards the eye, the eye having an eye axis, the eye axis defining a z-axis, the z-axis defining a plurality of xy-planes within the eye, the target comprising a vitreous eye floater;

receive the imaging beam reflected from the eye;

generate three-dimensional (3D) image data from the reflected imaging beam; and generate a plurality of two-dimensional (2D) enface images from the 3D image data by taking a slice of the 3D image data and summing, averaging, or projecting data of the slice to yield a 2D enface image, a 2D enface image imaging an xy-plane within the eye, the plurality of 2D enface images comprising at least one target enface image imaging the target in the eye and a retinal enface image imaging a retina of the eye, the retinal enface image showing a shadow cast by the target onto the retina;

a laser device configured to direct a laser beam along a laser beam path towards the target;

an xy-scanner configured to:

receive the imaging beam from the OCT device and direct the imaging beam along the imaging beam path towards the eye; and receive the laser beam from the laser device and direct the laser beam along the laser beam path aligned with the imaging beam path towards the eye; and a computer configured to:

compare the target of the target enface image and the shadow of the retinal enface image to confirm the presence of the target;

perform image processing on the target enface image to determine a feature of the target by:

performing image processing on the target enface image to identify an outline of the target and determining a size of the target from the outline of the target; and performing image processing on the target enface image to identify an outline of the target and determining a shape of the target from the outline of the target;

track the target according to the target enface image imaging the target;

track the target by tracking the shadow cast by the target according to the retinal enface image;

overlay an outline of the target onto the target enface image;

overlay a no-fire zone onto the target enface image; and generate a plurality of three-dimensional (3D) images from the 3D image data.

* * * * *